United States Patent [19]

Masel

[11] Patent Number: 5,674,067
[45] Date of Patent: Oct. 7, 1997

[54] FLAVORED ORTHODONTIC ELASTIC BAND AND METHOD OF TREATING ORTHODONTIC PATIENT

[76] Inventor: Richard I. Masel, 1809 Sadler Dr., Champaign, Ill. 61820

[21] Appl. No.: 485,806

[22] Filed: Jun. 7, 1995

[51] Int. Cl.$^6$ ................................................. A61C 3/00
[52] U.S. Cl. ........................... 433/24; 433/18; 433/2; 433/19
[58] Field of Search ........................... 433/23, 2, 18, 433/19, 22, 10, 11, 24; 132/321

[56] References Cited

U.S. PATENT DOCUMENTS

| | | |
|---|---|---|
| 822,309 | 6/1906 | William . |
| 3,205,576 | 9/1965 | Wallshein . |
| 3,600,807 | 8/1971 | Sipos . |
| 4,818,225 | 4/1989 | Fasnacht ................................. 433/18 |
| 5,080,583 | 1/1992 | Hunting ................................. 433/2 |
| 5,433,952 | 7/1995 | Sipos ................................. 424/489 |

FOREIGN PATENT DOCUMENTS

93/17633  9/1993  WIPO .

OTHER PUBLICATIONS

Kirk–Othmer, Concise Encyclopedia of Chemical Technology, John Wiley & Sons, Inc. (1985), pp. 1028–1036.

Kirk–Othmer, Concise Encyclopedia of Chemical Technology, John Wiley & Sons, Inc. (1985), pp. 391–400 and pp. 1036–1038.

*Primary Examiner*—Jeffrey A. Smith
*Attorney, Agent, or Firm*—Eckert Seamans Cherin & Mellott

[57] ABSTRACT

A flavored orthodontic elastic band has a substantially solid inner elastic band member for providing good tension characteristics, and a porous coating layer carrying a flavoring substance that is released upon exposure to saliva, for a predetermined time corresponding to the effective life of the elastic band member for exerting operative tension in an orthodontic fitting. The solid inner band is formed either in a general ring configuration, a series of interconnected rings configuration, or an elongated string configuration, or other configurations suitable for orthodontic application. The solid inner band is formed from natural rubbers, synthetic rubbers, thermoplastic elastomers, and blends thereof. The inner band member substantially determines the elasticity of the band, and is not flavored. The porous coating is applied over at least part of the solid core and can also include natural rubbers, synthetic rubbers, thermoplastic elastomers, and blends thereof. An effective amount of a soluble flavoring agent is incorporated in the coating layer to flavor the band and includes a flavoring oil, flavoring powder, and blends thereof, and is released from the porous elastic layer upon exposure to saliva, moisture, and/or acids in the patient's mouth. The flavoring substance preferably is dispersed in the outer porous elastic layer in an amount of about 0.1 to 20 percent by weight of the porous elastic layer. Multiple flavoring layers can also be provided having varying concentrations of flavoring substance therein to effect better control over the time release characteristics of the flavoring agent, such that the release of a constant and effective amount of flavoring substance occurs for a predetermined time, and thereafter the release rapidly drops off to impart little or no taste. Such an effect will alert the patient to replace the band. An effective amount of a swelling polymer can also be included in the outer porous elastic layer to induce additional porosity. An effective amount of a medicinal agent can further be included in the outer porous elastic layer in place of or in addition to the flavoring agent to provide a curative or soothing effect.

21 Claims, 2 Drawing Sheets

FLAVORED ORTHODONTIC ELASTIC BAND AND METHOD OF TREATING ORTHODONTIC PATIENT

1. FIELD OF THE INVENTION

The invention relates generally to orthodontic fittings, and in particular to orthodontic tensioning fittings used to move and align teeth. According to an aspect of the invention, an orthodontic elastic band with a resilient band member can be replaceably fixed by a patient in a stretched and tensioned condition in the patient's mouth to effect teeth alignment over time, and includes an added flavoring substance with a pleasant taste, encouraging frequent replacement by the patient and improved patient compliance with a prescribed treatment.

2. BACKGROUND OF THE INVENTION

Orthodontic bands of rubber and other elastic materials are conventionally used in the orthodontic profession to effect teeth movement over a period of time. Orthodontic elastic bands typically include a resilient band member made of an orally acceptable elastomeric material, for instance a natural or synthetic rubber, with added stabilizers, plasticizers, crosslinkers, colorants, and the like. Conventional orthodontic elastic bands may have no taste, or worse yet may have an unpleasant taste associated with the material of the rubber or plastic.

Orthodontic elastic bands are useful in a wide variety of orthodontic applications, including, without limitation, intraoral, extraoral, chained elastic, unicycle module and beta module applications (all for causing teeth to move), ligating module applications (for securing intraoral appliances), and elastic sleeving applications (for protecting arch wires and the like).

Intraoral elastic bands are particularly common. Patients undergoing corrective teeth-alignment treatment need to fix such intraoral bands, for example, to apply tension between respective hooks associated with the teeth or with structures attached to the teeth, to be moved over time. In particular, the intraoral band may be connected within a patient's mouth at one end over a hook on a bicuspid bracket supporting an upper arch wire and at another end to a hook on a bicuspid bracket supporting a lower arch wire. Intraoral elastic bands apply the necessary directional force to the teeth to urge the teeth to move toward their corrected positions. Patients are required to replace such intraoral elastic bands frequently, preferably several times each day, to maintain maximum tension. Frequent replacement of the elastic bands is critical to maintain the desired level of corrective force, because the elastic strength of the elastic band decays rather rapidly. This is due to material properties and also due to exposure to saliva, water, and acids in the mouth. The elastic modulus of certain common orthodontic elastic bands typically decays between about forty and sixty percent during the first two hours after such bands are placed in tension in the patient's mouth.

Patients often fail to replace their intraoral elastic bands until hours after their elastic strength has substantially degraded. Infrequent and/or irregular replacement deprives these patients of the proper corrective force and as a result, longer periods of treatment are required to achieve teeth alignment for non-compliant patients than for those that diligently and frequently replace their bands. It is a goal of the orthodontic profession to improve the regularity and frequency with which patients replace their orthodontic elastic or rubber bands, to ensure optimally effective and efficient orthodontic treatment.

Attempts have been made to solve the problem of patient non-compliance in replacing their orthodontic elastic bands, by providing flavored orthodontic elastic band compositions. Such bands have a characteristic pleasant tasting flavoring added to the resilient band member. Upon exposure to saliva and moisture in a patient's mouth, such flavored bands release the flavoring and thereby encourage more regular and frequent replacement. However such attempts have had their drawbacks.

U.S. Pat. No. 3,205,576 (Wallshein) discloses oral dispensing orthodontic elastic bands to be stretched between hooks in a patient's mouth to effect teeth alignment. In Wallshein, the elastic bands have a soluble oral dispensing substance incorporated in the resilient elastic member, which is released with saliva action. The soluble substance dispensed into the saliva may have anesthetic, medicinal, soothing or flavor action, such as anti-caries, stannous fluoride, benzocaine, sweetener and/or scent. Wallshein teaches that the elastic member made of rubber can be impregnated, coated or otherwise made with caches or shallow sockets or slits to carry a quantity of a medicinal or flavoring preparation, whereby expansion of the resilient member exposes the soluble preparation to saliva for releasing it. Wallshein further teaches that the soluble preparation, for instance, sodium or ammonium saccharin, cinnamon, aspirin, scented or flavored granules, can be incorporated in the material of the elastic member by impregnating the rubber mass during manufacture, by dipping, brushing, coating the surface of the elastic member, by depositing on the surface powdered masses in gum as a vehicle, or by making shallow sockets, slits, or other depressions to hold the preparations.

In Wallshein, the techniques taught of forming openings, depressions or the like for caches, and adding material to the mix of elastic material, both displace and tend to degrade the elastic material, thereby reducing the elasticity of the band. Depositing gum or a similar material on the surface also tends to affect elasticity. Insofar as openings for caches are provided or the surface may be sticky or irregular, sites are formed that tend to trap food particles and/or permit bacteria to grow. Therefore, the results are not entirely desirable.

U.S. Pat. No. 4,818,225 (Fasnacht) discloses another flavored orthodontic elastic band for intraoral use to increase the frequency of replacement and encourage patient compliance with a treatment program. In Fasnacht, the elastic bands consist of an orally acceptable elastomeric material, which can be a natural, natural-synthetic, or synthetic rubber, thermoplastic polymer, or blends thereof, and a homogeneously dispersed flavoring substance in the elastomeric material. The flavoring substance is uniformly dispersed in the elastomeric mass during compounding, and is released by contact with the oral environment. The flavoring substance can be provided in a liquid or powder form and may include flavoring oils, such as peppermint or spearmint oils, and artificial sweeteners, such as aspartame powders and powdered synthetic flavoring. The flavoring substance is dispersed in the elastomer in an amount of about 0.1 to 10 parts by weight per 100 parts of elastomeric material, preferably about 1 to 5 parts by weight flavoring substance. In Fasnacht, however, incorporation of the flavoring substance into the elastomeric material again tends to degrade the elastic properties of the band by displacing elastic material that in the absence of the added material would bind continuously. Furthermore, incorporation of the flavoring substance within the polymer matrix during plastic processing tends to prevent the release of the flavoring substance therefrom upon saliva action and, consequently, fails to effectively mask the unpleasant rubbery taste.

Another foreign reference describes a dispensing orthodontic rubber band with a two-part construction. This Intl. Pat. Appln. No. PCT/US93/01983 (Podell, et al.) discloses a two-part structure for adhesive bandages, dressings, sutures and the like, or for toothbrushes and orthodontic rubber bands, comprising a flexible elastomeric material, of rubber or latex, bonded to a hydrogel polymer coating, such as cellulose, polyurethane or polyacrylate base polymer. A soluble medicant or bactericide is bonded to the hydrophilic polymer coating to provide a slow release of medication upon contact with bodily fluids such as saliva. However, no flavoring agent is suggested. Also, the hydrogel polymer is not particularly flexible, such that the structure is more useful as a wound dressing than as an orthodontic rubber band.

Other U.S. patents disclose other types of orthodontic or dental appliances which have been imparted with a pleasantly scented or flavored taste.

U.S. Pat. No. 822,309 (Schrader) discloses a highly elastic rubber sheeting which is scented to release an agreeable odor during use by dentists as a rubber dam which is forced around a tooth under treatment so as to keep saliva from reaching a tooth cavity. In Schrader, the agreeable scents are provided by incorporating heliotropin, cumarin or nerolin, for example, in the rubber dam. The scent is uniformly distributed in the rubber mass and cured therein during vulcanization of the rubber, thus masking or eliminating the disagreeable odor of conventional vulcanized rubber.

U.S. Pat. No. 5,080,583 (Hunting) discloses a fragrant orthodontic appliance made by combining fragrancing oils with an acrylic monomer liquid, followed by combining the mixture with acrylic polymer powder to form a hard fragranced acrylic base member into which orthodontic hardware is embedded, such as an arch wire, to mount an orthodontic appliance. The fragrancing oils can be peppermint, lemon, grape, pineapple, watermelon and the like and are added to the acrylic monomer in a ratio between about 1:5 and 1:10 of fragrancing oil to monomer. Hunting provides a pleasant tasting and smelling orthodontic appliance which is intended to ameliorate the discomfort experienced by patients.

U.S. Pat. No. 3,600,807 (Sipos) discloses an oral dental apparatus for making the mouth pleasantly tasteful and for making exhaled air aromatically pleasant. The dental apparatus can be an artificial tooth having an opening, such as an aperture covered by a screen and filled with an absorbent fibrous material saturated with air-refreshant fluid, or a removable insert for containing such fluid. The air-refreshant fluid can be clove, peppermint or other pleasant tasting oil.

Despite the many prior attempts at providing flavored orthodontic fittings, in particular flavored orthodontic elastic bands, a more effective means would be advantageous to flavor the orthodontic fittings, in particular orthodontic elastic bands, while maintaining optimal structural and physical characteristics.

What is needed is an orthodontic elastic band wherein the flavoring substance is dispensably held but does not degrade the elastic properties of the band material.

3. SUMMARY OF THE INVENTION

It is an object of the invention to provide a flavored orthodontic elastic band having a dispensably held soluble flavoring substance while also having optimal elastic properties.

It is another object of the invention to encourage frequent and regular replacement by patients of their orthodontic elastic bands by providing a pleasantly tasting orthodontic elastic band which releases a soluble flavoring agent upon exposure to saliva in the patient's mouth without degrading the elastic properties of the band.

It is yet another object of the invention to allow for a controlled time release of the flavoring substance for a predetermined amount of time without degrading the elastic properties of the band.

These and other objects, features and advantages are accomplished according to the invention by a flavored orthodontic elastic band having a substantially solid inner elastic band member, for example a closed loop or ring with a circular cross section, made of an orally acceptable elastomeric material such as natural rubbers, synthetic rubbers, thermoplastic elastomers, and blends thereof. The inner band member substantially determines the elasticity of the band, and preferably is not flavored using cache openings or mixed flavorant material, so that maximum elasticity and strength are provided.

A thin outer porous elastic layer is applied over or formed integrally with the solid core and preferably includes a substantially porous orally acceptable elastomeric material such as natural rubbers, synthetic rubbers, thermoplastic elastomers, and blends thereof, and an effective amount of a releasable soluble flavoring agent such as a flavoring oil, flavoring powder, and blends thereof. The flavoring agent is released from the outer porous elastic layer upon exposure to saliva, moisture, and/or acids in the patient's mouth. The porous surface layer can be rendered porous by dispersing the flavoring agent in the elastomeric material or by caching the flavoring agent on the elastomeric material, or also by dispersing a polymer additive or blowing agent with the flavoring substance in the elastomeric material to further enhance porosity. The size of the pores contained in the outer layer is not in excess a size to trap and retain food.

By incorporating the flavoring agent in a thin outer porous layer, the band has excellent flavoring agent release properties defined by the porosity of the outer layer and also has excellent elasticity characteristics defined substantially by the core band. Furthermore, the release of the flavoring agent from the thin porous layer does not correspondingly cause the elastic properties of the core band to degrade. Moreover, the release of the flavoring substance through a thin layer is over a shorter time and slows more abruptly than release of comparable agent dispersed throughout an entire thickness of a band, which advantageously encourages the patient to change to fresh bands.

Multiple outer porous flavoring layers can also be provided to effect different release characteristics of the flavoring agent. For instance, successive outer porous layers, each layer having a concentration, which may vary, of flavoring agent associated therewith, can be applied over the solid core band. With use of successive porous flavored elastic layers, it is advantageous to include the flavoring agent in gradations in each layer, such that a constant release of the flavoring substance occurs for a predetermined period of time, and thereafter an abrupt drop off in release.

The outer porous elastic layer(s) can be bonded to or integrally formed with at least a portion of the outer surface of the inner elastic band member. The flavoring substance preferably is incorporated, preferably dispersed, in the outer porous elastic layer in an amount of about 0.1 to 20 percent by weight of the porous elastic layer, and can be the means by which the outer layer is rendered porous. With multiple layers, the flavoring substance is preferably provided in varying concentrations in each layer to effect a controlled release of the flavoring substance for a predetermined period of time and then an abrupt drop off thereafter. For instance, the greatest concentrations of flavoring substance can provided in the middlemost and outermost layers of the multiple porous elastic layers, with the middlemost layers preferably having a higher concentration than the outermost layers, and further with the least concentrations being provided in the innermost layers.

The outer porous elastic layer can be bonded to the inner elastic band member by coating the inner elastic band member or core with a latex solution comprised of a homogeneous mixture of the elastomeric material of the porous layer and flavoring substance and curing thereon. Polymer additives such as swelling agents and blowing agents can also be incorporated in the latex to enhance porosity. The outer porous elastic layer can also be formed on the elastic band core by immersing the core in an aqueous and flavoring substance solutions for an effective amount of time to integrally form an outer porous flavored layer on the core.

Additional aspects and advantages of the invention will be apparent from the following non-limiting discussion of preferred embodiments and examples.

4. BRIEF DESCRIPTION OF THE DRAWINGS

There are shown in the drawings certain exemplary embodiments of the invention as presently preferred. It should be understood that the invention is not limited to the embodiments disclosed, and is capable of variation within the spirit and scope of the appended claims. In the drawings.

5. DETAILED DESCRIPTION OF THE PREFERRED EMBODIMENTS OF THE INVENTION

An orthodontic rubber or other elastic band is used in a tensioned condition and secured between, for example, hooks mounted in an orthodontic patient's mouth, to move and align the teeth by application of tension over time. According to an inventive aspect, the orthodontic elastic band of the invention is flavored with a soluble flavoring substance and provided in a novel two-part or multi-part construction, intended to encourage regular and frequent replacement by patients, without significant degradation of the elastic properties of the resilient band member due to the flavoring substance.

The orthodontic elastic band of the invention comprises a substantially solid inner elastic core forming an resilient band member. The resilient band member is made of an orally acceptable elastomeric material which can be a natural rubber, synthetic rubber, thermoplastic elastomer, or blends thereof. The resilient band member is selected to have suitable elastic properties for application of the desired corrective force when used in a tensioned condition in a patient's mouth. The resilient band member can be provided in various strengths and sizes depending on the orthodontic application. Typical shapes of orthodontic bands include those in a ring, chain (i.e., a series of interconnected rings having generally smaller rings than a regular rubber band), or string configuration. Typical orthodontic ring dimensions are from about 1/16 to 1/2 inch in inner diameter and 3/32 to 5/8 inch in outer diameter.

An example of an acceptable natural rubber is cis-1,4-polyisoprene (polyisoprene) rubber. Examples of acceptable synthetic rubbers are isoprene rubber, butyl rubber, neoprene rubber, silicone rubber, acrylic rubber, butadiene rubber, styrene-butadiene rubber, nitrile-butadiene rubber, ethylene-propylene rubber, ethylene-propylene-diene rubber. Examples of acceptable thermoplastic elastomers are styrene-butadiene-styrene elastomer, styrene-isoprene-styrene elastomer, and thermoplastic polyurethane elastomer. Reference can be made to Kirk-Othmer, *Concise Encyclopedia of Chemical Technology*, John Wiley & Sons, Inc. (1985), pp. 391–400 and pp. 1036–1038, for a more detailed discussion of suitable natural, synthetic, and thermoplastic elastomers useful for the orthodontic band of the invention.

Other suitable additives can also be included in the elastomeric material of the resilient band member, such as reinforcers, fillers, plasticizers, softeners, extenders, and other processing aids, vulcanizing agents, cross-linking agents, catalysts, accelerators, retarders and other curative aids, colorants, antioxidants, antiozonants and other stabilizers, and surfactants and emulsifiers (for latex), as commonly used for rubber compounding and manufacture. Reference can be made to Kirk-Othmer, *Concise Encyclopedia of Chemical Technology*, John Wiley & Sons, Inc. (1985), pp. 1028–1036, for a more detailed discussion of specific rubber chemicals and compounding and processing techniques.

The orthodontic elastic band of the invention further comprises a substantially porous outer elastic member bonded to or integrally formed on the resilient band member of the solid core. The porous elastic member is also made of an orally acceptable elastomeric material which can be aforementioned natural rubber, synthetic rubber, thermoplastic elastomer, or blends thereof. The porous elastic member can be provided on a selected portion(s) of the solid core surface or, preferably, on the entire surface of the solid core. The porous elastic member preferably comprises a thin layer surrounding all outer surfaces of the solid core.

The outer porous elastic member contains a flavoring substance which can be impregnated, dipped, coated thereon, or mixed or dispersed therein. The flavoring substance is soluble and is released from the porous elastic member into a patient's mouth when exposed to moisture or saliva. The flavoring substance is provided in an effective amount to ensure release of the flavoring substance for a predetermined period which corresponds to a nominal useful life of the orthodontic elastic band, namely a period during which the core member maintains substantial tension. Thus the dissipation of the flavoring substance corresponds to the time the band should be replaced by the patient. Termination of the release of flavoring substance thereby encourages replacement of the band at the appropriate time. The flavoring substance is also provided in an effective amount to induce a porous or rough elastomer matrix to form as the outer layer.

The flavoring substance can be selected from pleasant tasting natural or synthetic flavoring oils or powders. Examples of acceptable flavoring oils are peppermint, spearmint, grape, lemon, orange, or other mints and fruits, and the like. Examples of acceptable flavoring powders are artificial sweeteners such as saccharin, aspartame, bubble gum, and the like. Other known and acceptable natural and artificial flavoring substances can be used as well. Also, the flavoring substance can be combined or substituted with other commonly known water soluble dispensing agents, such as medicinal, anti-microbial, bactericide, or soothing agents and the like, if desired.

The flavoring substance is preferably present in the outer porous elastic member in an amount of about 0.1 to 20% by weight per porous elastomeric material, more preferably about 0.5 to 5% by weight, most preferably about 1 to 2% by weight. The outer porous elastic member layer containing the flavoring substance is preferably provided as a thin coating layer on or within the solid core, preferably from about 100 to 1250 microns (0.0004 to 0.005 inch) thick, more preferably about 200 to 1000 microns (0.0008 to 0.004 inch) thick, most preferably about 500 to 750 microns (0.002 to 0.003 inch) thick.

In addition, multiple substantially porous outer elastic layers containing flavoring substance may be provided, to provide for more controlled and effective release characteristics of the flavoring substance therefrom. The multiple layers preferably range from about 2 to 10 layers, more preferably from about 2 to 5 layers, most preferably 3 layers. The multiple outer porous layers can be applied over the solid core band in succession, with each layer having concentrations of flavoring agent which may vary in gradations, to provide for a constant release of the flavoring substance to occur for a predetermined period of time corresponding to the useful life of the orthodontic elastic band, and thereafter to have an abrupt drop off in release. For instance, the greatest concentrations of flavoring substance can provided in the middlemost and outermost layers of the multiple porous elastic layers, with the middlemost layers preferably having a higher concentration than the outermost layers, and further with the least concentrations being provided in the innermost layers. In a three outer porous layer arrangement bonded to the solid core, the concentration gradient of the flavoring agent in the porous layers can be set up as middlemost layers>topmost layers>bottommost layers. In a three layer arrangement, for example, each layer may be from about 250 to 750 microns (0.001 to 0.003 inch) thick, and, from bottom to top, may contain about 0.5%, about 3%, and about 2%, all by weight, flavoring substance, respectively.

The porosity of the outer elastic coating is preferably provided in a range from about 1 to 10% void volume, preferably about 2 to 3% void volume, but most preferably provided with sufficient porosity to allow for effective diffusion of the flavoring substance therefrom in an oral environment. The outer elastic coating material can be rendered porous by the inclusion of the flavoring substance in the elastomeric mass during compounding and applying as a latex solution on the core, by solubilizing soluble components within the surface region of the core matrix and replacing with flavoring substance, or by other means. Inclusion of a blowing agent or swelling agent as well in the elastomeric mass during processing can enhance the porosity. The porosity of the elastic coating material provides greater surface area for saliva to contact and enhances release of flavoring substance. However, the pore sizes should not be greater than about 0.1 to 200 microns (0.0000004 to 0.0008 inch) in diameter, but most preferably not greater than a size which will trap and retain food particles or the like therein, which is undesirable.

The porous elastic member can contain other swelling agents or polymer additives, such as carboxymethyl cellulose and other cellulose derivatives, polyvinyl alcohol and other polyvinyl alcohol derivatives, polyacrylamide and other polyacrylamide derivatives, and other polymers which swell in water and are orally acceptable, to induce porosity in the porous elastic member. These swelling agents tend to swell upon contact with moisture or saliva in a patient's mouth. Consequently, when such additives are incorporated into the porous elastic member and exposed to moisture or saliva, the additives swell and tend to create additional pores or pockets in the elastic. These pores provide for enhanced diffusion of the flavoring substance from the elastic member, but also are filled with swelled polymer such that no food particles can be trapped or retained. The porous elastic layer preferably can comprise about 0.1 to 5% by weight polymer swelling agent, preferably about 0.5 to 3% by weight.

As preferably constructed, the orthodontic elastic band of the invention comprises an inner solid elastic band core, and bonded to or formed on the core, an outer porous elastic member having a swelling agent and flavoring substance dispersed therein. The inner solid elastic band core allows the orthodontic elastic band to maintain its elastic properties without degradation as a result of a flavoring substance incorporated therein. Moreover, the outer porous elastic member allows the flavoring agent to be released over a predetermined amount of time in a patient's mouth while not adversely affecting the elastic properties of the solid core. In addition, as preferably constructed, the orthodontic elastic band of the invention comprises an inner solid elastic band core, and bonded to the core, multiple outer porous elastic members, most preferably three, having a swelling agent and flavoring substance, preferably in varying concentrations, dispersed therein. The multiple porous elastic members allow for a substantially constant release of the flavoring substance to occur for a predetermined period of time corresponding to the useful life of the orthodontic elastic band, and thereafter to abruptly drop off in release to signal to the patient, via substantially no more flavored taste, to replace the band.

In preparing the flavored orthodontic elastic band of the invention, the solid elastic band core is first provided. Off the shelf elastics can be used for the core which can be of any suitable shape, size and strength as are commonly known for orthodontic applications. Otherwise, various methods can be used to make orthodontic elastic bands as are well known. For example, individual bands can be cut from elongated tubes of elastomeric material by conventional rubber processing techniques such as dipping a mandrel into a suitable tank containing liquid rubber latex dispersion comprising rubber and conventional rubber additives, for instance, vulcanizers, accelerators, emulsifiers, emulsion stabilizers, antioxidants, etc. as are well known, and then curing (i.e., via emulsion-polymerization) or otherwise by dry mixing rubber and conventional rubber additives, and then forming by extruding, molding, injection molding, etc., followed by curing. After curing, the elongated tubes are cut into the desired thickness to form bands. Reference can be made to U.S. Pat. No. 4,818,225 (Fasnacht) for a more detailed description of elastic band processing techniques, the disclosure of which is hereby incorporated.

After the inner solid elastic band or core has been provided, then the outer porous elastic member containing a releasable flavoring substance is bonded thereto or integrally formed on the surface thereof. In the bonding method, a latex rubber dispersion comprising rubber and conventional rubber additives which further includes the flavoring substance, e.g., fruit or mint flavoring oil or powder, uniformly dispersed therein are provided in a suitable tank. Then by preferably using a dipping process, the solid elastic band core on a mandrel is dipped into the dispersion of rubber latex and flavoring substance such as a flavoring oil, and cured thereon by conventional methods. Again, reference can be made to U.S. Pat. No. 4,818,225 (Fasnacht) for a more detailed description of latex dipping and curing techniques, as well as extruding and curing techniques. Each dip after cure typically provides an outer rough and porous layer from about 125 to 750 microns (0.0005 to 0.003 inch) thick, preferably between from about 250 to 750 microns (0.001 to 0.003 inch) thick, the amount primarily dependant upon the nature of the latex blend. Porosity of the outer layer is enhanced by incorporating an effective amount of swelling agent, e.g., polyvinyl alcohol, carboxymethyl cellulose, and the like, or blowing agent in the latex dispersion to form cells or voids in the polymer matrix.

In the integral outer layer forming method, the solid band core is first placed in a suitable tank containing water and soaked therein for an effective amount of time, typically 8 to 24 hours, to solubilize water soluble components contained in the elastic matrix and remove these components from the core, thereby creating voids or pores on the surface of the core. Also by soaking the core in water, a substantially all of the unpleasant rubbery flavor is removed from the core as well. Then, the solid band core is placed in a suitable tank containing a solution of flavoring substance, such as flavoring oil or flavoring powder in vegetable oil, e.g., linseed oil, or other suitable solution, and soaked therein for an effective amount of time, typically about 10 minutes to 5 hours, to allow the flavoring substance to coat the surface of the core and diffuse in the near surface region of the core, thereby integrally forming an outer porous layer containing flavoring substance. The amount of time of exposure of the core in the flavoring solution is adjusted to allow the flavoring substance to be effectively incorporated into the surface of the core while leaving the core and its elastic properties intact. In addition, the solid core can also be soaked in a swelling agent solution, e.g., polyvinyl alcohol or carboxymethyl cellulose, to increase the porosity of the outer surface containing flavoring substance. Next, the resultant layered core is removed from the flavoring solution and dried.

These methods provide a porous elastic coating with flavoring substance generally surrounding the outer surface of the solid band core. This porous elastic coating is thin in comparison to the dimensions of the core, which allows the elastic band to stretch and deform substantially to the same extent as an uncoated band, since the coating is also flexible.

The coating releases the flavoring substance by diffusion through the porous matrix upon exposure to saliva, while the inner core allows the orthodontic elastic band to maintain the required elastic properties. Successive coats can also be made to provide a multi-layered embodiment to effect different release properties to the porous elastic layer.

Figure 1:
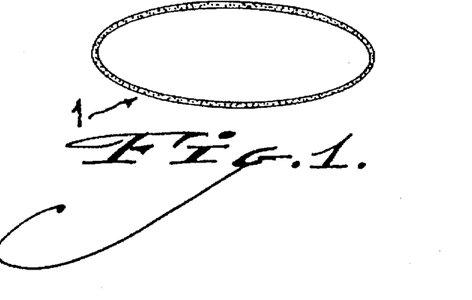
FIG. 1 is a perspective view of the flavored orthodontic elastic band of the invention.
Figure 2:
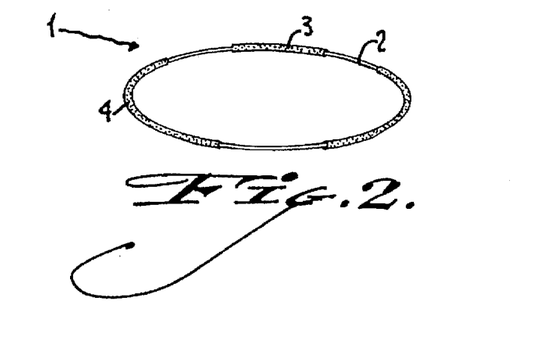
FIG. 2 is a perspective view of the flavored orthodontic rubber band of the invention of FIG. 1 partially cut away at a portion.
Figure 3:
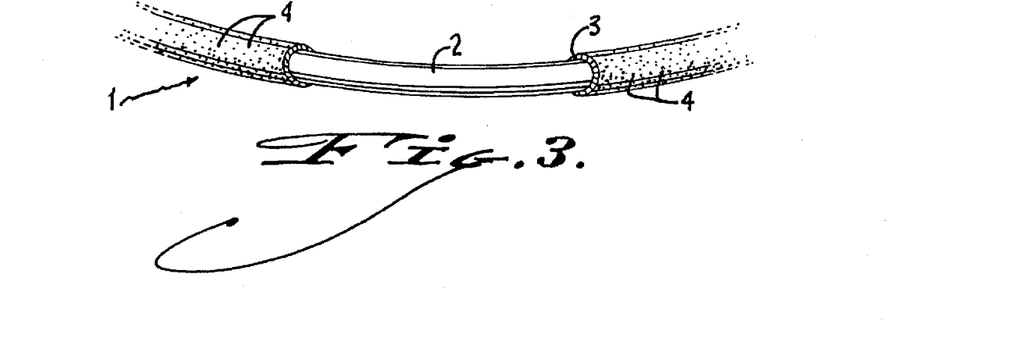
FIG. 3 is a side fragmentary view of the flavored orthodontic elastic band of the invention of FIG. 1 partially cut away at a portion.
Figure 4:
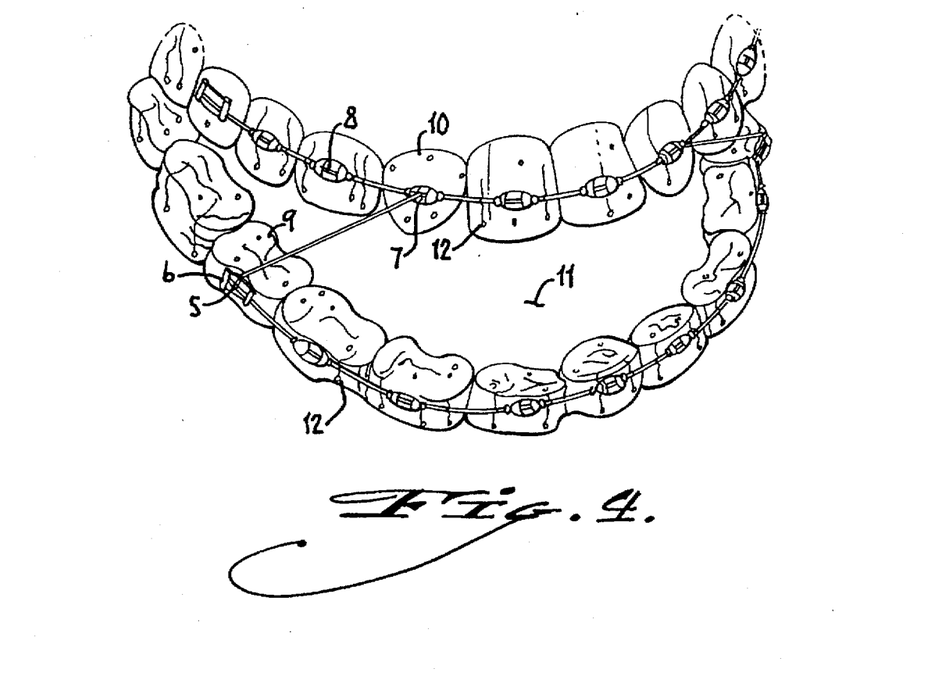
FIG. 4 is a side view of an orthodontic patient's mouth having the flavored orthodontic elastic band of the invention secured therein. Upon contact with saliva or moisture, the orthodontic rubber band releases flavoring substance to the oral environment.

Referring now to the drawings, FIGS. 1–3 show one embodiment of the flavored orthodontic elastic band of the invention as a two-part intraoral band, and FIG. 4 shows this flavored orthodontic rubber band secured in a patient's mouth to effect teeth movement and enhance regular and frequent replacement by the patient through incorporation of a pleasant tasting flavoring substance without correspondingly degrading the elastic properties of the elastic band. In FIGS. 1–3, the orthodontic rubber band (1) comprises a substantially solid, i.e., substantially non-porous, elastic band core (2) and coated on the outer surface of the core (2) is a porous elastic layer (3) containing a soluble flavoring substance (4). As shown in FIG. 4, the flavored orthodontic elastic band (1) is secured in a tensioned condition between a hook (5) supported on a lower tooth bracket (6) and another hook (7) supported an upper tooth bracket (8), both brackets being bonded to selected teeth (9) and (10) in a patient's mouth (11). Upon contact with saliva or moisture (12) in a patient's mouth, the orthodontic rubber (1) band releases flavoring substance (4) from the porous elastic layer (3) to the oral environment.

Figure 5:
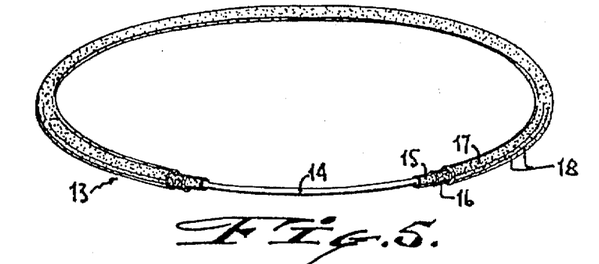
FIG. 5 is a perspective view of another embodiment of the flavored orthodontic elastic band of the invention partially cut away at a portion.
Figure 6:
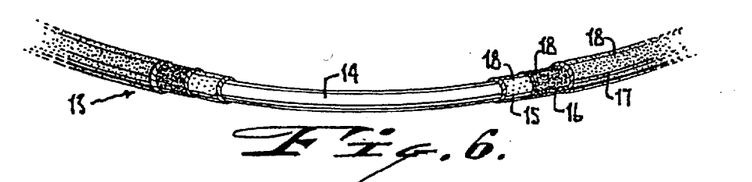
FIG. 6 is a side fragmentary view of the flavored orthodontic elastic band of the invention of FIG. 5 partially cut away at a portion; and, FIG. 7 is a graphical illustration of the concentration gradients of the flavoring substance of an exemplary flavored orthodontic elastic band of the type as shown in FIG. 5.
Figure 7:
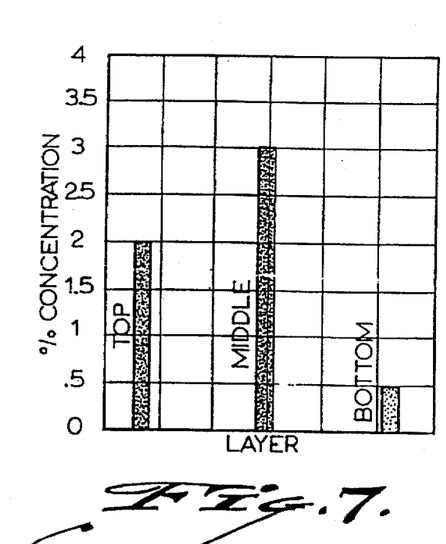

In a still another preferred embodiment, several different porous layers, preferably three separate layers, are applied successively to the solid core, using repeated latex dipping and curing steps as previously described, and varying the concentrations of flavoring substance and swelling polymers in the latex solution, thereby changing the time release characteristics of the rubber band. Referring again to the drawings, FIGS. 5 and 6 show an embodiment of the flavored orthodontic elastic band of the invention having three porous elastic layers coated on the solid band core. As shown, the orthodontic rubber band (13) comprises a substantially solid, i.e., substantially non-porous, elastic band core (14) and coated on the outer surface of the core are three successive outer porous elastic layers (15), (16) and (17) from bottom to top, with each respective layer containing a soluble flavoring substance (18), preferably in varying amounts, and as shown in FIG. 7, having a flavoring substance concentration gradient of middle layer (16) greater than top layer (17) much greater than bottom layer (15).

Figure 8:
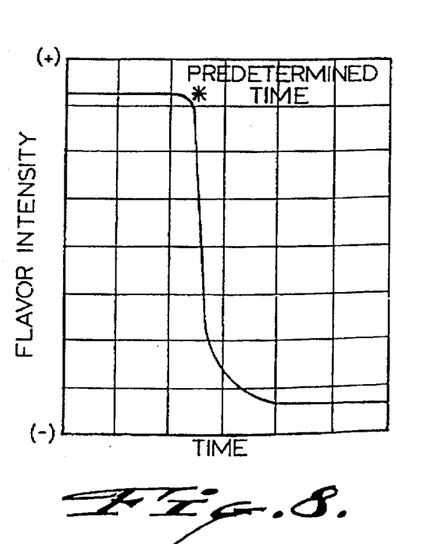
FIG. 8 is a graphical illustration of the release characteristics of the flavoring substance of an exemplary flavored orthodontic elastic band of the type as shown in FIG. 5.

As shown in FIG. 8, the time release characteristics of an exemplary three layered orthodontic elastic band of type as shown in FIG. 5 is designed to release an effective amount of flavoring substance for a predetermined time corresponding to the useful life of the elastic band, which is determined by the time the elastic properties of the band diminish below a threshold correct force required to be applied to the teeth to effect teeth movement, and thereafter to rapidly reduce the release of flavoring substance to a minimal value, thereby imparting little or no more flavored taste to a patient's mouth and consequently signalling the patient to replace the band with a new band.

The invention will now be clarified by a consideration of the following example, which is intended to be purely exemplary of the flavored orthodontic of the invention.

EXAMPLE 1

Two-Part Flavored Orthodontic Elastic Band by Dipping and Curing

A two-part flavored orthodontic rubber band was formed by providing an orthodontic rubber band comprising about a 1.6 by 0.74 mm (0.063×0.029 inch) solid band core of natural rubber having an internal diameter of about 9.5 mm (0.375 inch) which was coated on its outer surface with about 750 microns (0.003 inch) thick porous elastic layer using a dipping process in a latex solution containing a mixture of the natural rubber and flavoring substance, as well as vulcanizers, emulsifiers, and other standard rubber chemicals used for latex rubber processing and then curing. In particular, the latex solution contained about 97% by weight natural rubber (polyisoprene) latex, about 0.9% by weight sulfur vulcanizer, about 0.6% by weight zinc oxide, about 1% by weight antioxidant, and about 0.5% by weight accelerator. Added to the latex dispersion was a flavoring substance containing about 3% by weight peppermint flavored oil, 2% by weight peppermint powder. The composite orthodontic band was then cured by conventional techniques.

EXAMPLE 2

Four-Pan Flavored Orthodontic Elastic Band by Dipping and Curing

A four-part flavored orthodontic rubber band was formed by providing an orthodontic rubber band comprising about a 1.6 by 0.74 mm (0.063×0.029 inch) solid band core of natural rubber having an internal diameter of about 9.5 mm (0.375 inch) which was coated on its outer surface with three successive about 250 microns (0.001 inch) thick porous elastic layers, one on top of each other, using three consecutive dipping and curing processes in three different latex dispersions. Each latex dispersion contained a mixture of the natural rubber and varying amounts of flavoring substance, as well as vulcanizers, emulsifiers, and other standard rubber chemicals used for latex rubber processing and then curing by conventional techniques. In particular, each latex solution contained about 97% by weight natural rubber (polyisoprene) latex, about 0.9% by weight sulfur vulcanizer, about 0.6% by weight zinc oxide, about 1% by weight antioxidant, and about 0.5% by weight accelerator. A flavoring substance was added in varying concentrations to each of the three consecutive latex dispersions. The latex dispersion for the first dipped layer contained approximately 0.5% by weight, for the second dipped layer contained approximately 3% by weight, and for the last dipped layer contained approximately 2% by weight flavoring agent. The flavoring agent was a mixture of flavoring oil and flavoring powder which included 3 parts of peppermint flavored oil to 2 parts of peppermint powder.

EXAMPLE 3

Two-Part Flavored Orthodontic Elastic Band by Integrally Forming a Layer on Core A two-part flavored orthodontic rubber band with about a ⅜th inch inner diameter, about 0.030 inch thick solid rubber core, and about 0.002–0.003 inch (500 to 750 microns) thick outer porous layer containing flavoring agent was prepared. The preparation included soaking a Masel 5002-403 rubber band in room temperature water for about 18 hours to extract the soluble proteins and other water soluble components from the rubber band. This produced a substantially flavorless, i.e., non-rubbery tasting, rubber band with pores formed on the surface where the soluble substances had been removed. The rubber band was then air dried for about 24 hours. After drying, the rubber band was then soaked for about 2 hours in an Otten 3266 bubble gum flavor. The bubble gum flavor soaked into the outer 0.002–0.003 inch (500 to 750 microns) thickness of the rubber band but left the core of the rubber band intact.

EXAMPLE 4

Two-Part Flavored Orthodontic Elastic Band with Additional Porosity

A solid natural rubber tube with about a ⅜th inch inner diameter and about a 0.032 inch wall thickness from Kent latex was dipped into a bath containing a latex dispersion of about 50% water and 47% natural rubber latex (50% solids) dispersion, 1.4% carboxymethyl cellulose, 0.45% sulfur vulcanizer, 0.3% zinc oxide, 0.5% antioxidant, 0.25% accelerator, and 0.1% flow enhancer. The tube was removed from the bath, heated to about 100° F. to cure and dry the rubber, and then washed in hot water. This process was repeated twice to produce about a 0.002 inch (500 microns) thick porous layer on the solid core. The resultant tube was then cut into about 0.0625 inch slices to form orthodontic bands and then flavored by soaking in water, drying, and soaking in flavoring agent using the procedure described in Example 3. The carboxymethyl cellulose coating produced an outer layer on the rubber band core with additional porosity and flavoring substance.

EXAMPLE 5

Three-Part Flavored Orthodontic Elastic Band with Additional Porosity

A solid natural rubber tube with about a ⅜th inch inner diameter and about a 0.032 inch wall thickness was dipped into a bath containing a latex dispersion of about 50% water and 46% natural rubber latex (50% solids) dispersion, 2.4% carboxymethyl cellulose, 0.45% sulfur vulcanizer, 0.3% zinc oxide, 0.5% antioxidant, 0.25% accelerator, and 0.1% flow enhancer. The tube was removed from the bath, heated to about 100° F. to cure and dry the rubber, and then washed in hot water. This produced a solid band core with about a 0.001 inch (250 microns) thick porous outer layer. The resultant tube was then coated again with another 0.001 inch (250 microns) thick porous outer layer and subsequently flavored using a single cycle of the procedure in Example 4. A resultant ⅜th inch inner diameter solid rubber core with two porous 0.001 inch (250 microns) thick outer layers with flavoring substance was produced.

This invention disclosure incorporates by reference herein all of the aforementioned U.S. patent and other references in their entireties.

The invention having been disclosed in connection with the foregoing variations and examples, additional variations will now be apparent to persons skilled in the art. The invention is not intended to be limited to the variations and examples specifically mentioned, and accordingly reference should be made to the appended claims rather than the foregoing discussion of preferred embodiments, to assess the spirit and scope of the invention in which exclusive rights are claimed.

I claim:
1. A flavored orthodontic elastic band which comprises:
   an inner substantially solid elastic band member comprised of an orally acceptable elastomeric material selected from the group consisting of natural rubber, synthetic rubber, thermoplastic elastomers, and blends thereof; and,
   an outer relatively porous elastic layer having pores smaller than about 0.1 to 200 microns in diameter, whereby the porous elastic layer substantially excludes food particles, said porous elastic layer bonded to at least a portion of at least one surface of the inner band member, the porous elastic layer comprising an orally acceptable elastomeric material selected from the group consisting of natural rubber, synthetic rubber, thermoplastic elastomers, and blends thereof, and having an effective amount of a releasing agent comprised of an orally acceptable soluble flavoring substance selected from the group consisting of flavoring liquids, flavoring powders, and blends thereof, the porous elastic layer releasing the flavoring substance upon exposure to saliva in an orthodontic patient's mouth.

2. The flavored orthodontic elastic band of claim 1, in which the inner solid elastic band member has a shape selected form the group consisting of a general ring shape, a chain shape comprising a series of interconnected rings, and an elongated string shape.

3. The flavored orthodontic elastic band of claim 1, in which the outer porous elastic layer is bonded to at least a portion of the outer surface of the inner elastic band member.

4. The flavored orthodontic elastic band of claim 1, in which the outer porous elastic layer is bonded to the outer surface of the inner elastic band member.

5. The flavored orthodontic elastic band of claim 1, in which the outer porous elastic layer is bonded to both inner and outer surfaces of the inner elastic band member.

6. The flavored orthodontic elastic band of claim 1, in which the flavoring substance is incorporated in the outer porous elastic layer in an amount of about 1 to 20% by weight of the outer porous elastic layer.

7. The flavored orthodontic elastic band of claim 1, in which the inner elastic band member has a general ring shape or chain shape comprising a series of interconnected rings, each ring having a dimension between about 1/16 and 1/2 inch in inner diameter and between about 3/32 to 5/8 inch in outer diameter, and the outer porous elastic layer with flavoring agent bonded thereto having about 0.0005 to 0.005 inch in thickness.

8. The flavored orthodontic elastic band of claim 1, in which the amount of porosity the outer porous elastic layer defined by the void volume is about 1 to 10% void volume.

9. The flavored orthodontic elastic band of claim 1, in which the outer porous elastic layer is bonded to the inner elastic band member by coating onto the inner elastic band member, a latex solution comprised of a homogeneous mixture of the elastomeric material of the porous layer and flavoring substance, and curing, or by immersing the inner elastic band member in water and then in flavoring substance.

10. The flavored orthodontic elastic band of claim 1, in which the inner elastic band member comprises a natural rubber and the outer porous elastic layer comprises a natural rubber.

11. The flavored orthodontic elastic band of claim 1, in which the outer porous elastic layer comprises multiple layers of the same with varying effective amounts of flavoring substance, for controlling the predetermined time of release therefrom.

12. The flavored orthodontic elastic band of claim 1, in which the flavored orthodontic elastic band is an intraoral elastic band used in a tensioned condition in an orthodontic patient's mouth.

13. The flavored orthodontic elastic band of claim 1, in which the outer porous elastic layer further comprises an orally acceptable swelling polymer.

14. The flavored orthodontic elastic band of claim 13, in which the swelling polymer is selected from the group consisting of carboxymethyl cellulose, other cellulose derivatives, polyvinyl alcohol, other polyvinyl alcohol derivatives, polyacrylamide and other polyacrylamide derivatives.

15. The flavored orthodontic elastic band of claim 13, in which the swelling polymer is provided in a concentration of from about 0.1 to 5% by weight of the outer porous elastic layer.

16. A flavored orthodontic elastic band which comprises:
an inner substantially solid elastic band member having a general ring shape, interconnected ring shape, or elongated string shape and comprised of an orally acceptable elastomeric material selected from the group consisting of natural rubber, synthetic rubber, thermoplastic elastomers, and blends thereof, the solid elastic band member providing effective elastic behavior for exerting tension in an orthodontic fitting; and
multiple successive outer substantially porous elastic layers bonded to at least a selected portion of at least one surface of the inner band member, each of the layers independently comprised of an orally acceptable elastomeric material selected from the group consisting of natural rubber, synthetic rubber, thermoplastic elastomers, and blends thereof, and each layer having an effective amount of a releasing agent comprised of an orally acceptable soluble flavoring substance selected from the group consisting of flavoring liquids, flavoring powders, and blends thereof, incorporated in the porous elastic layer, for releasing the flavoring substance from the porous elastic layers upon exposure to saliva, moisture, and acids in an orthodontic patient's mouth, and further comprised of an effective amount of an orally acceptable swelling polymer, for swelling and inducing porosity upon exposure to saliva, moisture, and acids in an orthodontic patient's mouth.

17. The flavored orthodontic elastic band of claim 16, in which each successive outer layer comprises diminishing amounts of releasing flavoring substance from the outermost to innermost successive layers which controls the release of the flavoring substance through the outermost porous layer for a predetermined time, and abruptly reduces the release after the predetermined time.

18. The flavored orthodontic elastic band of claim 16, which comprises between about 3 to 10 layers, and in which each successive outer layer comprises varying amounts of flavoring substance in a concentration gradient set up as middle layer≧top layer>>bottom layer.

19. The flavored orthodontic elastic band of claim 18, in which the concentration of flavoring substance in the bottom layer comprises about 0.1 to 2% by weight, the middle layer preferably comprises about 1 to 5% by weight, and the top layer comprises about 1 to 5% by weight.

20. The flavored orthodontic elastic band of claim 16, in which each successive layer further comprises from about 0.5 to 5% by weight of a swelling polymer additive selected from the group consisting of carboxymethyl cellulose, other cellulose derivatives, polyvinyl alcohol, other polyvinyl alcohol derivatives, polyacrylamide and other polyacrylamide derivatives.

21. A method of treating an orthodontic patient, which comprises:
placing in an orthodontic patient's mouth and securing between hooks supported on brackets around teeth, a flavored orthodontic elastic band comprised of an inner, relatively solid, elastic band member having a general ring shape, interconnected ring shape, or elongated string shape and comprised of an orally acceptable elastomeric material selected from the group consisting of natural rubber, synthetic rubber, thermoplastic elastomers, and blends thereof, which exhibits effective elastic behavior, and bonded to at least a selected portion of at least one surface of the inner band member, an outer, relatively porous, elastic layer having pores smaller than about 0.1 to 200 microns in diameter, whereby the porous elastic layer substantially excludes food particles, said porous elastic layer being comprised of an orally acceptable elastomeric material selected from the group consisting of natural rubber, synthetic rubber, thermoplastic elastomers, and blends thereof, and dispersed or incorporated in the porous elastic layer, an effective amount of a releasing agent comprised of an orally acceptable soluble flavoring substance selected from the group consisting of flavoring liquids, flavoring powders, and blends thereof, which releases from the porous elastic layer upon exposure to saliva, moisture, and acids in an orthodontic patient's mouth;

maintaining the flavored orthodontic elastic band in position for a predetermined period of time to apply the desired corrective force on the teeth to effect teeth movement;

removing the flavored orthodontic elastic band from securement after said predetermined period of time; and replacing the removed orthodontic elastic band with an unused orthodontic elastic band of the same composition in a patient's mouth and securing between hooks supported on brackets around teeth, in which method the elastic properties of the orthodontic elastic band are not substantially degraded by the release of flavoring substance therefrom.

* * * * *